(12) United States Patent
Collins et al.

(10) Patent No.: US 6,716,356 B2
(45) Date of Patent: Apr. 6, 2004

(54) THERMALLY ENHANCED DIALYSIS/DIAFILTRATION SYSTEM

(75) Inventors: Gregory R. Collins, Monroe, NY (US); James Summerton, Park Ridge, NJ (US); Edward Spence, Bronx, NY (US)

(73) Assignee: Nephros, Inc., New York, NY (US)

( * ) Notice: Subject to any disclaimer, the term of this patent is extended or adjusted under 35 U.S.C. 154(b) by 138 days.

(21) Appl. No.: 10/009,450

(22) PCT Filed: Jan. 11, 2001

(86) PCT No.: PCT/US01/01024
§ 371 (c)(1),
(2), (4) Date: Dec. 6, 2001

(87) PCT Pub. No.: WO01/51185
PCT Pub. Date: Jul. 19, 2001

(65) Prior Publication Data
US 2002/0158019 A1 Oct. 31, 2002

Related U.S. Application Data

(60) Provisional application No. 60/175,579, filed on Jan. 11, 2000.

(51) Int. Cl.[7] .......................... B01D 61/24; B01D 61/26; B01D 61/28

(52) U.S. Cl. .................. 210/646; 210/195.2; 210/321.6; 210/321.71; 210/321.72; 210/433.1; 210/434; 210/645; 210/739; 210/805; 210/175

(58) Field of Search .......................... 210/85, 87, 194, 210/195.2, 321.6, 321.71, 321.72, 321.75, 321.84, 433.1, 434, 645, 646, 647, 739, 175, 805; 422/44; 604/4.01, 5.01

(56) References Cited

U.S. PATENT DOCUMENTS

| 3,579,441 A | 5/1971 | Brown |
| 3,878,095 A | 4/1975 | Frasier et al. .................. 210/87 |

(List continued on next page.)

FOREIGN PATENT DOCUMENTS

| EP | 0 018 734 | 11/1980 |
| EP | 0 076 422 | 4/1983 |

(List continued on next page.)

OTHER PUBLICATIONS

Basile, Carlo et al., Plasma Volume Changes induced by Hypertonic Hemodiafiltration and Standard Hemodialysis, Am. J. Nephrol. 7: 264–269 (1987).

(List continued on next page.)

*Primary Examiner*—John Kim
(74) *Attorney, Agent, or Firm*—Darby & Darby

(57) ABSTRACT

The present invention provides a hemodialysis or hemodiafiltration system and method using two dialyzer stages (122, 138), wherein the temperature of a dialysate fluid stream of the first cartridge (122) is increased such that the blood in the first cartridge (122) is dialyzed or diafiltered at an elevated temperature, while blood in the second cartridge (138) is dialyzed or diafiltered against a dialysate stream at normal blood temperature. This results in an increased solute diffusivity and a corresponding increase in removal of blood substances by diffusion. When diafiltration is performed, an additional removal of substances occurs by convection as a larger portion of plasma water from a blood compartment (142) can be filtered across a semi-permeable membrane (140) at the same transmembrane pressure due to the reduced viscosity of the heated blood and plasma water.

24 Claims, 2 Drawing Sheets

U.S. PATENT DOCUMENTS

| | | | |
|---|---|---|---|
| 3,946,731 A | 3/1976 | Lichtenstein | 128/214 R |
| 3,976,576 A | 8/1976 | Jacobsen et al. | 210/321 |
| 4,038,190 A | 7/1977 | Baudet et al. | 210/321 |
| 4,118,314 A | 10/1978 | Yoshida | 210/22 |
| 4,134,834 A | 1/1979 | Brous | 210/127 |
| 4,219,422 A | 8/1980 | Knothe et al. | 210/137 |
| 4,381,999 A | 5/1983 | Boucher et al. | 210/637 |
| 4,498,990 A | 2/1985 | Shaldon et al. | 210/637 |
| 4,647,378 A | 3/1987 | Minami | 210/646 |
| 4,702,829 A | 10/1987 | Polaschegg et al. | 210/195.2 |
| 4,708,802 A | 11/1987 | Rath et al. | 210/641 |
| 4,722,798 A | 2/1988 | Goss | 210/646 |
| 4,739,492 A * | 4/1988 | Cochran | 210/321.71 |
| 4,770,769 A | 9/1988 | Schael | 210/96.2 |
| 4,834,888 A | 5/1989 | Polaschegg | 210/646 |
| 4,861,485 A | 8/1989 | Fecondini | 210/641 |
| 4,894,164 A * | 1/1990 | Polaschegg | 210/646 |
| 4,908,014 A * | 3/1990 | Kroyer | 604/113 |
| 5,011,607 A | 4/1991 | Shinzato | 210/637 |
| 5,069,788 A | 12/1991 | Radovich et al. | 210/321.8 |
| 5,075,003 A | 12/1991 | Aoyagi | 210/321.8 |
| 5,178,763 A | 1/1993 | Delaunay | 210/644 |
| 5,194,157 A | 3/1993 | Ghezzi et al. | 210/646 |
| 5,211,849 A | 5/1993 | Kitaevich et al. | 210/645 |
| 5,244,568 A | 9/1993 | Lindsay et al. | 210/87 |
| 5,318,750 A | 6/1994 | Lascombes | 422/81 |
| 5,431,811 A | 7/1995 | Tusini et al. | 210/90 |
| 5,476,592 A | 12/1995 | Simard | 210/651 |
| 5,487,827 A | 1/1996 | Peterson et al. | 210/87 |
| 5,511,875 A | 4/1996 | Jonsson et al. | 366/136 |
| 5,578,223 A | 11/1996 | Bene et al. | 210/85 |
| 5,660,722 A * | 8/1997 | Nederlof | 210/90 |
| 5,690,831 A | 11/1997 | Kenley et al. | 210/646 |
| 5,700,372 A | 12/1997 | Takesawa et al. | 210/321.81 |
| 5,702,597 A | 12/1997 | Chevallet et al. | 210/195.2 |
| 5,711,883 A | 1/1998 | Folden et al. | 210/646 |
| 5,725,775 A | 3/1998 | Bene et al. | 210/646 |
| 5,808,181 A | 9/1998 | Wamsiedler et al. | 73/38 |
| 5,846,419 A | 12/1998 | Nederlof | 210/323.1 |
| 5,871,694 A | 2/1999 | Beden et al. | 422/44 |
| 6,039,877 A | 3/2000 | Chevallet et al. | 210/636 |

FOREIGN PATENT DOCUMENTS

| | | |
|---|---|---|
| EP | 0 516 152 | 12/1992 |
| EP | 0 715 859 * | 6/1996 |
| EP | 0 890 368 | 1/1999 |
| EP | 0 960 624 | 12/1999 |
| WO | WO 92/11878 | 7/1992 |
| WO | WO 98/16171 | 4/1998 |
| WO | WO 98/16269 | 4/1998 |
| WO | WO 98/35710 | 8/1998 |
| WO | WO 98/50090 | 11/1998 |
| WO | WO 00/44478 | 8/2000 |

OTHER PUBLICATIONS

Basile, Carlo, et al., Hypertonic hemodiafiltration: A preliminary report on a cross–over study, Kidney International, vol. 33, Suppl. 24, pp. S–132–S–134 (1988).

Canaud, B,. et al., Hemodiafiltratyion with On–Line Production of substitution Fluid: Long–Term Safety and Quantitative Assessment of Efficacy, Maeda K. Shinzato T (eds): Effective Hemodiafiltration: New Methods. Contrib Nephrol. Basel, Karger, vol. 108. pp 12–22 (1994).

Ghezzi, P.M. et al., Hemodiafiltration 'Without Replacement Fluid, ASAIO Journal, 61–65 (1992).

Ghezzi, P.M. et al., Use of the ultrafiltrate obtained in two–chamber (PFD) hemodiafiltration as replacement fluid. Experimental ex vivo and in vitro study. The International Journal of Artificial Organs/vol. 14/No. 6, 1991/pp. 327–334.

Kim, Sung–Teh, Characteristics of Protein Removal in Hemodiafiltration, Maeda K. Shinzato T (eds): Effective Hemodiafiltration: New Methods. Contrib Bephrol. Basel, Karger, vol. 108, pp. 23–37, (1994).

Maeda, Kenji, et al., Push/Pull Hemodiafiltration: Technical Aspects and Clinical Effectiveness, Nephron 71:1–9 (1995).

Man, N. K., et al., Acetate–Free Biofiltration: State of the Art, Hemodiafiltration: New Methods. Contrib Nephrol. Basel, Karger, vol. 108, pp. 87–93 (1994).

Marangoni Roberto, et al., Short Time Treatment with high–Efficiency Paired Filtration Dialysis for Chronic Renal Failure, Artificial Organs, 547–552, Blackwell Scientific Publications, Inc., Boston International Society for Artificial Organs (1992).

Miller, J. H., et al., Technical Aspects of High–Flux Hemodiafiltration for Adequate short (Under 2 Hours) Treatment, the Department of Medicine, Wadsworth V.A. medical Center, and UCLA school of; medicine, Los Angeles, California, pp. 377–380, (1984).

Ono Masataka, et al. Comparison of Types of On–line Hemodiafiltration from the Standpoint of Low–Molecular–Weight Protein Removal, Contrib Nephrol. Basel, Karger, vol. 108. pp 38–35 (1994).

Ronco, C. et al., Comparison of four different short dialysis techniques. The International Journal Of Artificial Organs/vol. 11/No. 3, pp 169–174, (1988).

Ronco, C. et al., Paired Filtration dialysis: Studies on Efficiency, Flow Dynamics and Hydraulic Properties of the System, Blood Purif 8:126–140, (1990).

Ronco, C. et al., Technical and Clinical Evaluation of Different short, Highly Efficient Dialysis Techniques, Contr. Nephrol., vol. 61, pp. 46–68 (Karger, Basel 1988).

Sanz–Moreno C. et al., Hemodiafiltration in Two Chambers Without Replacement Fluid: A Clinical Study. Artificial Organs, 19(5): 407–410, Blackwell Science, Inc., Boston International Society for Artificial Organs (1995).

Shinaberger James H. et al., Short Treatment 16: pp. 360–381 (undated).

Shinzato, et al., Newly Developed Economical and Efficient Push/Pull Hemodiafiltration, Maeda K. Shinzato T (eds): Effective Hemodiafiltration: New Methods. Contrib Nephrol Basel, Karger, vol. 108, pp. 79–86 (1994).

Sternby Jan, A Decade of Experience with On–Line Hemofiltration/Hemodiafiltration, Maeda K. Shinzato T (eds): Effective Hemodiafiltration: New Methods. Contrib Nephrol Basel, Karger, vol. 108, pp. 1–11 (1994).

Tsuruta Kazuma, A Simple Method for Clinical Application of Push/Pull Hemodiafiltration, Maeda K. Shinzato T (eds): Effective Hemodiafiltration: New Methods. Contrib Nephrol Basel, Karger, vol. 108, pp. 71–78 (1994).

Usuda M., et al., New Simultaneous HF and HD With No Infusion Fluid, vol. XXV111 Trans Am Soc Artif Intern Organs, pp. 24–25, (1982).

Vanholder, et al., In vivo solute elimination of paired filtration dialysis. The International Journal of Artificial Organs/vol. 14/No. 1, pp. 23–27 (1991).

Wizemann V., et al., On–Line haemodiafiltration versus low–flux haemodialysis. A prospective randomized study, Nephrol Dial Transplant 15 [suppl 1]: 43–38, (2000).

Zucchelli P., Paired Filtration Dialysis: Optimizing Depurative Efficiency with Separate Convection and Diffusion Processes, Nephron 56: 166–173 (1990).

Ahrenholz R. et al., On–line hemodiafiltration with pre– and postdilution: a comparison of efficacy. The International Journal of Artificial Organs/Vol 20/No 2, pp. 81–90 (1997).

Shinzato T. et al., Infusion–free Hemodiafiltration: Simultaneous Hemofiltration and Dialysis with No Need for Infustion Fluid, Artificial Organs, vol. 6, pp. 453–456 (1982).

* cited by examiner

THERMALLY ENHANCED DIALYSIS/DIAFILTRATION SYSTEM

This application is a U.S. national phase application under 35 U.S.C. §371 of co-pending International application Serial No. PCT/US01/01024, filed Jan. 11, 2001, which claims the benefit of U.S. patent application Ser. No. 60/175,579, filed Jan. 11, 2000, both of which are incorporated herein by reference in their entirety. The International application was published in the English language, as International Publication Number WO 01/51185 on Jul. 19, 2001.

FIELD OF THE INVENTION

This invention relates to dialysis and hemodiafiltration in general and, more particularly, to improved hemodiafiltration methods and devices for removal of blood toxins.

BACKGROUND OF THE INVENTION

Hemodialysis and Hemodiafiltration are well known methods for removing toxic substances from a patient's blood, thereby reducing the level of toxins in the patient's blood as part of an extracorporeal blood cleansing system. Both these methods are based on flowing blood through a cartridge containing a semi-permeable membrane which separates the cartridge into two compartments. In general, hemodialysis is a process whereby blood flows through a blood-side compartment of the cartridge, while a cleansing solution, i.e., a dialysate solution, flows through a dialysate-side compartment of the cartridge. Toxins are removed from the blood by diffusion across the semi-permeable membrane from the blood-side compartment to the dialysate-side compartment. The rate of diffusion is determined by the concentration gradient established between a higher concentration of toxins in the blood relative to the dialysate fluid. Hemodiafiltration is process whereby the normal removal of toxins by diffusion is augmented by a convective flow of plasma water across the semi-permeable membrane which assists in carrying toxins by bulk flow of fluid from the bloodside of the membrane to the dialysate side of the membrane. The transportation of plasma water across the semi-permeable membrane is achieved by establishing a pressure gradient, generally referred to as Transmembrane Pressure (TMP), across the membrane. In hemodiafiltration, an equivalent amount of a substitution fluid, or replacement fluid, must be added to the blood to replace the plasma water that is filtered across the membrane. This substitution fluid is generally added either before the blood enters the cartridge (pre-dilution mode) or after the blood exits the cartridge (post-dilution mode).

Hemodiafiltration systems using two cartridges connected in series are also known in the art. In such systems, a first cartridge is used as a conventional diafiltration cartridge providing simultaneous diffusion and filtration of plasma water across the semi-permeable membrane. In a second cartridge, toxins are diffused from the blood to the dialysate fluid, and a reverse pressure gradient is used to reverse-filter dialysate fluid from the dialysate-side compartment, across the membrane, and into the blood-side compartment. The reverse-filtered dialysate fluid serves as a substitution fluid to replace the amount of plasma water that filtered from the blood-side compartment to the dialysate-side compartment in the first cartridge. Such a method is described in J. H. Miller et al., "Technical Aspects of High-Flux Hemodiafiltration for Adequate Short (Under 2 Hours) Treatment," Transactions of American Society of Artificial Internal Organs (1984), pp. 377–380.

SUMMARY OF THE INVENTION

It is an object of this invention to provide a method and a system using two dialyzes or diafiltration cartridges, or two stages of a single dialyzer cartridge, whereby the temperature of the dialysate fluid entering the first cartridge is increased above the normal dialysate temperature. The increased temperature increases the solute diffusivity, or diffusion coefficients, thereby enhancing the removal of substances by diffusion in the first dialyzer stage. Another advantageous result of increasing the dialysate temperature is that the viscosity of the blood is decreased, thereby enhancing the filtration of plasma water across the semipermeable membrane for a given transmembrane pressure in the first dialyzer stage. This enhances the removal of solutes by convection as the increased bulk flow of plasma water carries additional toxic substances. In the second dialyzer stage, e.g., a second dialyzer cartridge, the blood temperature is decreased back to its normal level, e.g., by heat exchange and/or by addition of substitution fluid at normal blood temperature.

The present invention provides a hemodialysis or hemodiafiltration system and method using two dialyzer stages, e.g., two dialyzer cartridges connected in series, wherein the temperature of the dialysate fluid stream of the first dialyzer is increased such that the blood in the first cartridge is dialyzed or diafiltered at an elevated temperature, while blood in the second cartridge is dialyzed or diafiltered against a dialysate stream at normal blood temperature (i.e. at approximately 35° C. to 40° C.). The second cartridge may serve to correct for blood temperature shifts caused by high dialysate temperature in the first cartridge, and to further remove blood toxins by diffusion or diafiltration against a at normal blood temperature. In hemodialysis applications, transfer of heat from the higher temperature blood to the lower temperature dialysate in the second cartridge may assist in correcting (i.e., lowering) the blood temperature. In hemodiafiltration applications, the blood temperature may be lowered before the second dialyzer stage by adding substitution fluid into the blood stream.

The present invention may be embodied in an improved dialysis machine that includes means for heating a portion of the dialysate fluid path above normal blood temperature, e.g., above 40° C. Such a machine may include other components used in dialysis machines, such as a water preparation module to degas and heat water necessary for preparing dialysate, an ultrafiltration control system that may include a flow balancing system and an ultrafiltration (UF) pump, a dialysate proportioning system that introduces dialysate concentrates into the water stream, and an extracorporeal monitoring and control devices which may includes a blood pump for circulating blood through an extracorporeal circuit.

In some embodiments of the invention, the system is also designed to perform hemodiafiltration, and additional components may be used. For example, the system may include a substitution fluid supply system including a pump and substitution fluid filters for preparing substitution fluid "on-line" using a supply of dialysate fluid. The system may also include an interdialysate flow control system, which may including interdialysate pump, to regulate the relative ultrafiltration rates of the two dialyzer cartridges.

A hemodialysis/hemodiafiltration system and method using two cartridges connected in series is disclosed in PCT Application No. PCT/US99/25804 entitled "Non-Isosmotic Diafiltration System" filed in the name of Collins et al., the entirety of which is incorporated herein by reference. In the system of Collins et al., the dialysate fluid in the first cartridge is made hypertonic or hypotonic, by appropriately adjusting the electrolyte levels of the dialysate stream, to improve toxin removal efficiency.

BRIEF DESCRIPTION OF THE DRAWINGS

Further aspects of the instant invention will be more readily appreciated upon review of the detailed description of the preferred embodiments included below when taken in conjunction with the accompanying drawings, of which.

DETAILED DESCRIPTION OF THE INVENTION

Figure 1:
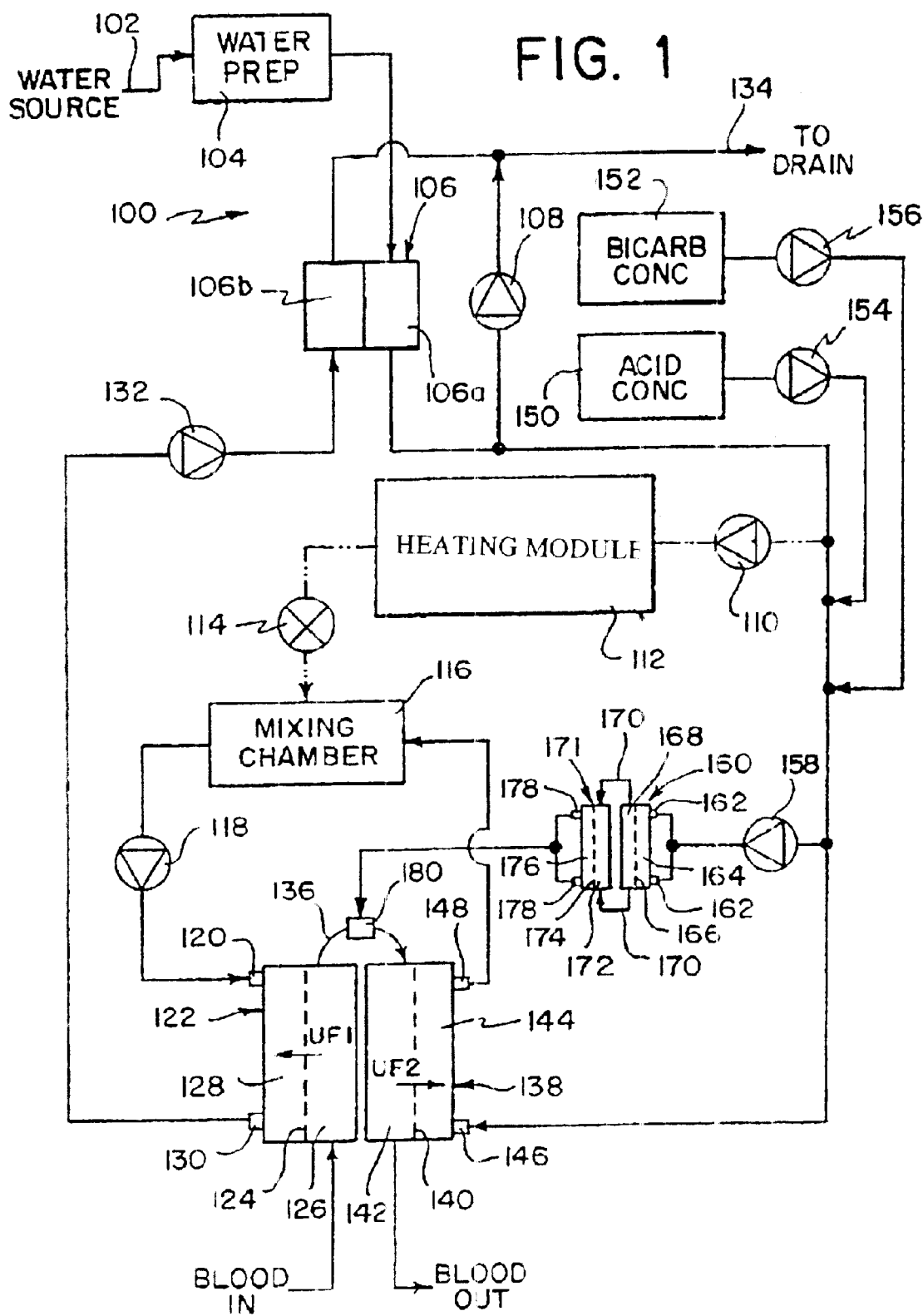
FIG. 1 is a schematic diagram illustrating a multistage, thermally enhanced, hemodiafiltration system in accordance with one embodiment of the present invention.
Figure 2:
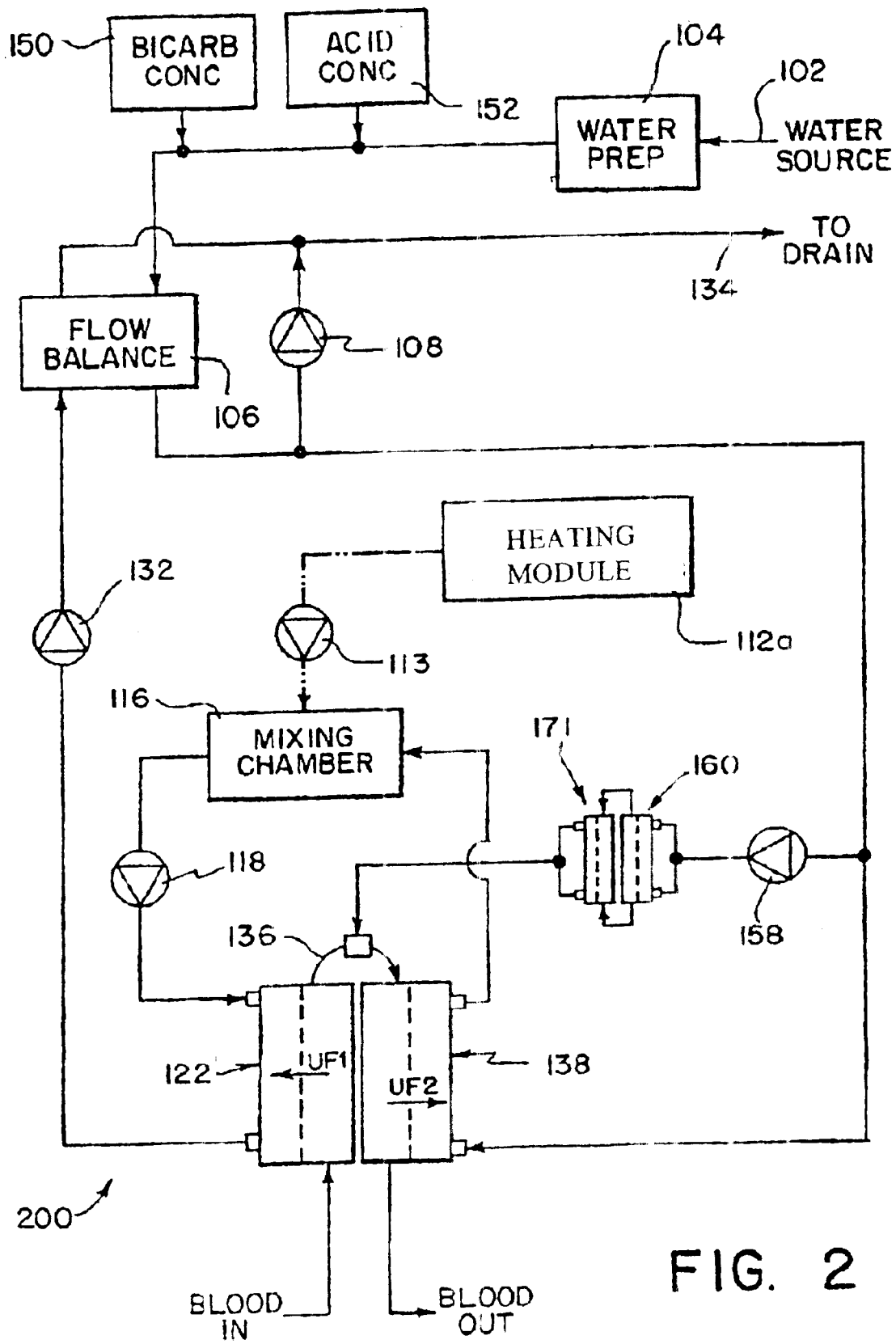
FIG. 2 is a schematic diagram illustrating a multistage, thermally enhanced, hemodiafiltration system in accordance with another embodiment of the present invention.

Referring now to FIGS. 1–2, wherein similar components of the instant invention are referenced in like manner, a preferred apparatus for thermally enhanced dialysis/diafiltration, and accompanying methods for using the same, are disclosed.

Turning now to FIG. 1, depicted therein is a first embodiment of a hemodialysis/diafiltration device which uses an internal heating system. A water source 102 supplies water or other base fluids, such as saline, to system 100 in order to create dialysate, substitution fluids and the like. The water, or other fluid is then provided to a water preparation module 104 which pre-treats the incoming fluid by heating, degassing and/or any other suitable method known to one of ordinary skill in the art.

The pre-treated fluid is next transported via appropriate tubing or the like to a flow balance system 106 which has an inlet controller 106a and outlet controller 106b, which in turn may continuously monitor and adjust flow rates of fluids entering or exiting the internal components of system 100. Flow balance system 106 may contain one or more microprocessor controls and the like which are programmed to automatically accomplish this functionality within pre-defined parameters.

The pre-treated fluid is transported first to internal components of system 100 through inlet controller 106a. A portion of the pre-treated fluid equivalent to the net amount of fluid to be removed from the patient may be siphoned through an ultrafiltration pump 108 to a drain 134. A remaining portion of pre-treatment fluid is next transported via appropriate tubing or the like to an auxiliary pump 110.

Pump 110 transports a pre-determined portion of the pre-treated fluid to a heat control module 112 which includes mean for controllably heating the pre-treated fluid, to form a heated solution which is provided to a first dialyzer cartridge 122, as described below. Pump 110 may be controlled by, for example, a microprocessor controller which is programmed to accept a predetermined portion of pre-treated fluid for creating the heated solution. Alternatively, the flow through pump 110 may be manually monitored and adjusted as needed.

The desired heating of the dialysate at module 112 may be achieved by adding a secondary fluid stream at an elevated temperature or by passing the fluid stream through a heating element in module 112 before the dialysate fluid is introduced into the dialyzer cartridge.

The heated solution flows from module 112 to an auxiliary valve 114. Valve 114 may likewise be automatically or manually controlled to allow a predetermined rate of heated solution to flow therethrough. The heated solution then flows to a mixing chamber 116. The mixing chamber 116 has a second inlet which receives dialysate solution from outlet port 148 of a second dialyzer cartridge 138, described further below. Mixing chamber 116 may be automatically or manually monitored and adjusted to allow a predetermined amount of heated solution to flow to an inlet port 120 of first dialyzer cartridge 122 via an interdialysate pump 118.

A remaining portion of the pre-treated fluid which is not accepted through pump 110 is transported to an inlet port 146 of second dialyzer cartridge 138. This fluid is not heated and is at preferably at temperature level lower than normal blood temperature. The system 100 may be provided with monitoring means for determining the appropriate temperature that is required to return blood treated in first dialyzer cartridge 122 to a normal temperature level, e.g., 35° C.–40° C. Pre-treated fluid at the desired temperature is provided to second dialyzer cartridge 138 via an inlet port 146. In an embodiment of the invention, an acid pump 154 and/or a bicarbonate pump 156 may be employed to pull acid concentrate 150 or bicarbonate concentrate 152 to adjust the pH of the remaining pre-treated fluid prior to providing the fluid to inlet 146.

Blood to be cleaned is received from a patient and enters the first dialyzer cartridge 122. The blood is carried by suitable tubing, as is known in the art, for example, blood-line tubing made from flexible polyvinylchloride (PVC). The flow rate of incoming blood is generally in the range of 100 to 600 ml/min, preferably 200 to 500 ml/min. First dialyzer cartridge 122 contains a semi-permeable membrane 124 that divides the dialyzer cartridge 122 into a bloodside compartment 126 and a dialysate compartment 128. As blood passes through bloodside compartment 126, plasma water containing blood substances is filtered across semi-permeable membrane 124. At the same time, the heated dialysate received from dialysate port 120 flows through dialysate compartment 128 in a direction counter to the blood flow. Blood substances and toxins are transferred across semi-permeable membrane 124 by diffusion due to a difference in concentration between the blood in blood compartment 126 and the dialysate in dialysate compartment 128. The dialysate containing blood substances and toxins removed from the blood is transported to drain 134 via dialysate pump 132 and outlet controller 106b.

In accordance with an embodiment of the invention, as blood flows through the blood compartment of the first dialyzer cartridge, the blood temperature is elevated. This results in an increased solute diffusivity and a corresponding increase in the removal of blood substances by diffusion. When diafiltration is performed, an additional removal of substances may occur by convection as a larger portion of plasma water from the blood compartment can be filtered across the semi-permeable membrane at the same transmembrane pressure due to the reduced viscosity of the heated blood and plasma water.

The partially dialyzed blood then exits first dialyzer cartridge 122 through a conduit 136. The blood then flows through conduit 136 and enters a bloodside compartment 142 of second dialyzer cartridge 138. The second dialyzer cartridge preferably contains a semi-permeable membrane 140 which divides the second dialyzer cartridge 138 into the bloodside compartment 142 and a dialysate compartment 144. As the blood passes through bloodside compartment 142, plasma water containing blood substances is filtered across the semi-permeable membrane 140. The temperature of the treated blood is returned to a desired level due to the difference in temperature between the blood in bloodside compartment 142 and the lower temperature dialysate flowing into dialysate compartment 144 through inlet port 146. Cleansed blood then exits the second dialyzer cartridge 138 and is recycled to the patient (not shown) through suitable tubing, for example, bloodline PVC tubing, as is known in the art. The dialysate exits the dialysate compartment 144 of second dialyzer cartridge 138 through outlet port 148 and is provided to mixing chamber 116, described above.

Additionally or alternatively, upon exiting the first dialyzer cartridge 122, the partially dialyzed/diafiltered blood may be mixed with a substitution fluid at normal blood temperature which helps reduce the temperature of blood in the second dialyzer cartridge 138. The temperature of dialysate flowing through the second dialyzer cartridge 138 may increase as heat is transferred from the higher temperature blood to the lower temperature dialysate.

Dialyzer cartridges 122 and 138 may be of any type suitable for hemodialysis, hemodiafiltration, hemofiltration, or hemoconcentration, for example, the Fresenius F60, available from Fresenius Medical Care, Lexington, Mass., the Baxter CT 110, available from Baxter Health Care, Deerfield, Ill., the Minntech Hemocor HPH 400, available from Minntech Corporation, Minneapolis, Minn., or the Hospal Filtral 16, available from Hospal A. G., Switzerland. Membranes 124, 140 are preferably medium or high flux membranes, for example, the polysulfone, cellulose triacetate or acrylonitrile membranes available from Fresenius Medical Care, Lexington, Mass., Minntech Corporation, Minneapolis, Minn., Baxter Health Care, Deerfield, Ill., or Hospal A. G., Switzerland.

In an embodiment of the present invention in which diafiltration is desired, the blood may be mixed with sterile substitution fluid between the first and second dialyzer cartridges at an inlet 180 of conduit 136 to form a blood/substitution fluid mixture. One way to accomplish this is disclosed in PCT Application No. PCT/US99/17468 entitled "Method for Efficient Diafiltration" filed in the name of Collins et al., the entirety of which is hereby incorporated by reference. Collins et al. uses two cartridges connected in series to perform forward filtration of plasma water from the blood compartment to the dialysate compartment in both cartridges simultaneously. Substitution fluid is added directly into the blood after it exits the first cartridge 122 and before it enters the second cartridge 138.

In the present invention, preparation of a sterile substitution fluid may be performed by filtration of a portion of pre-treated dialysate which is received from inlet controller 106a through substitution filter pump 158. The pre-treated dialysate flows across at least two filter membranes 166, 174 with a preferred molecular weight cut-off of not more than 40,000 Daltons. To accomplish this, a portion of the fresh dialysate solution may be split off the dialysate fluid stream at some point prior to entering dialysate compartment 144 of the second dialyzer cartridge 138. The split-off portion of the dialysate solution may flow through a conduit or the like which leads to a substitution fluid pump 158. Substitution fluid pump 158 generates the needed pressure to force the fluid down a conduit into inlet ports 162 of a first substitution fluid filter cartridge 160.

First substitution filter cartridge 160 contains the semi-permeable membrane 166 that separates the filter cartridge 160 into an upstream compartment 164 and a downstream compartment 168. First upstream compartment 164 has inlet ports 162. First downstream compartment 168 has one or more outlet ports connected to conduits 170. The substitution fluid from first downstream compartment 168 flows into a second substitution fluid cartridge 171 containing the semi-permeable membrane 174 which separates second substitution fluid cartridge 171 into a second upstream compartment 172 and a second downstream compartment 176. The sterile substitution fluid exits second substitution fluid cartridge 171 through second outlet ports 178 and is mixed with blood exiting first cartridge 122 to form the blood/substitution fluid mixture described above.

The pre-treated dialysate not used as substitution fluid enters the second dialyzer cartridge 138 through inlet port 146 of dialysate compartment 144, and flows counter-parallel to the blood flow as it traverses through bloodside compartment 142.

During diafiltration, excess plasma water filters across semi-permeable membrane 140 and mixes with the dialysate fluid, so as to maintain a patient's "dry weight" as the treated blood is infused. The dialysate fluid together with the filtered plasma water exits the second dialyzer cartridge 138 at outlet port 148, through a tube or conduit which directs the fluid to the mixing chamber 116, described above.

FIG. 2 depicts a thermally-enhanced hemodialysis/diafiltration system 200 in accordance with another embodiment of the present invention. The system 200 functions in a similar manner to system 100 except that heated dialysate fluid of a desired temperature is provided from heating module 112 directly to first dialyzer cartridge 122, via interdialysate pump 118, rather than being mixed within the machine as in system 100 of FIG. 1.

In this embodiment, the entire "partially spent" dialysate stream exiting second dialyzer cartridge 138 passes through heating module 112 to increase its temperature. The heating module may include any type of heating element, such as an electrical heating element, microwave energy, heat exchanger, etc. The heated dialysate stream then flows toward the dialysate inlet 120 of first dialyzer cartridge 122. Means for controlling the relative amounts of plasma water filtered off in the two cartridges 122, 138 (denoted as UF1 and UF2 in the drawings) may be used in both the embodiment of FIG. 1 and the embodiment of FIG. 2. For example, interdialysate pump 118 may include a servo-controlled pump which changes speed in accordance with control signals calculated based on the measured pressure differential, namely, the transmembrane pressure (TMP) across the semi-permeable membranes of the first and/or second dialyzers.

The partially spent, heated, dialysate fluid may then enters the dialysate inlet 120 of the first dialyzer cartridge 122. As the dialysate flows through the first cartridge 122, blood toxins and filtered plasma water accumulate in the fluid and heat is transferred from the higher temperature dialysate to the lower temperature blood. This raises the blood temperature having the effect of enhancing removal by diffusion, due to increased solute diffusivity, and by convection, due to higher filtration of lower viscosity plasma water. The spent dialysate fluid exits the first dialyzer cartridge 122 and flows back toward the flow balance chamber 106, and eventually to drain 134. It should be noted that some of the heat of the spent dialysate fluid stream may be recovered and used to partially heat the incoming water using an inlet water heat exchanger (not shown), as is known in the art.

The dialysis/diafiltration methods and devices of the invention as described above may be used as an add-on type system in conjunction with an existing ultrafiltration-controlled dialysis machine. However, it should be appreciated that the dialysis/diafiltration methods and devices of the present invention can also be embodied in a unitary, stand-alone dialysis/diafiltration machine.

In one embodiment of the present invention, the dialysis/diafiltration device includes first and second dialyzer cartridges 122, 138. Alternatively, a single cartridge having first and second separate dialyzer sections may be used.

The device may also include at least one sterility filter 160, 171, which may contain semi-permeable membranes. The sterility filter(s) 160, 171 are operative to remove bacteria, endotoxins, and other particulate from the dialysate, thereby generating a suitable substitution fluid stream on-line. A sterile/non-pyrogenic substitution fluid for use in conjunction with the present invention may be prepared by drawing a portion of fresh dialysate solution from a dialysate inlet line and pumping it through one or more sterile filter cartridge 160, 171. In an embodiment of the present invention, the sterile filter cartridges 160, 171 perform at least a double filtration of the dialysate solution before the solution is introduced into the blood as a substitution fluid. This double filtration can be performed by two separate ultrafiltration cartridges or a single cartridge that has multiple sections to perform multiple filtration of the substitution fluid. The use of multiple filtration to generate the on-line substitution fluid makes the system of the present invention safer, should one of the filters fail during treatment.

During operation of one embodiment of the present invention, blood enters a blood side compartment 126 of first dialyzer cartridge 122, whereby a portion of plasma water is filtered across the semi-permeable membrane 124 into the adjacent dialysate compartment 128. As the blood leaves the first dialyzer cartridge 122, substitution fluid may be added to the blood at a rate higher than the rate at which blood is filtered out of the first dialyzer cartridge 122. The diluted blood may then enter the bloodside compartment 142 of the second dialyzer cartridge 138, whereby additional plasma water (equal to the excess amount of substitution fluid) is filtered across the semi-permeable membrane 140 and into the adjacent dialysate compartment 144. In this manner, the substitution fluid acts as a post-dilution fluid relative to the first dialyzer cartridge 122 as well as a pre-dilution fluid relative to the second dialyzer cartridge 138.

The dialysate fluid may be generated by a dialysis machine, or by any other method known to one of ordinary skill in the art. In an embodiment of the present invention, the dialysate fluid enters the second dialyzer cartridge 138 and runs counter-parallel to the blood flow direction. The dialysate fluid acts to provide a concentration gradient against the bloodside fluid thereby facilitating the diffusion of solutes across the semi-permeable membrane 140, as described above. As the dialysate traverses through the dialysate compartment 144, the dialysate flow rate increases due to plasma water filtering across into the dialysate compartment 144, as mentioned above. Upon exiting the dialyzer cartridges 122, 138, the used dialysate may be transported back either to the dialysis machine (not shown) or to drain 134.

It should be apparent to those skilled in the art that this method can be performed with at least two dialyzer cartridges operating in a typical dialysis mode or it can be performed with two high flux dialyzer or diafiltration cartridges in a hemodiafiltration mode. The limiting factor being the capacity of the second cartridge acting as a heat exchanger to return the blood back to within a normal temperature range. In a diafiltration mode, substitution fluid is introduced into the blood steam between the two cartridges. The substitution fluid assists in restoring a normal blood temperature range in addition to the cooling being performed, by heat-exchange, at the second dialyzer cartridge.

The dialysis machine (not shown) used in conjunction with the present invention may perform all of its normal functions, such as preparing dialysate, metering dialysate flow rate, monitoring pressures, controlling net ultrafiltration, monitoring used dialysate for blood presence, etc. The diafiltration add-on system operates in conjunction with the dialysis machine, whereby the dialysate fluid from the dialysis machine is redistributed by the hemodiafiltration add-on system to its respective dialyzer and sterile filter cartridges. The fluid handling components of the diafiltration add-on system may be integrated with a microprocessor unit for controlling and executing the diafiltration aspect of the treatment.

The temperature of the pre-heated dialysate fluid used in conjunction with any of the embodiments described above is controlled by heating control module 112 and may be set to any desired temperature higher than normal blood temperature, e.g., higher than 40° C. The preferred temperature may depend on specific system parameters, for example, the dialysate flow rate and/or pressure and the blood flow rate and/or pressure. The heated dialysate temperature should also be controlled so as not to exceed a temperature that may cause damage to the blood being treated.

The systems disclosed in the foregoing may contain further pumps, monitoring devices, valves, electronic components, controllers, connector fittings, tubing, etc., as required in order to coordinate the operation of the system components.

Although the invention has been described in detail in the foregoing embodiments, it is to be understood that they have been provided for purposes of illustration only and that other variations both in form and detail can be made thereupon by those skilled in the art without departing from the spirit and scope of the invention, which is defined solely by the appended claims.

What is claimed is:

1. A blood cleansing system comprising: a source of dialysate fluid; a heating control module which receives dialysate fluid from said source and produces heated dialysate fluid; a first dialyzer including a first semi-permeable membrane that defines a first blood compartment and a first dialysate compartment, the first blood compartment having a first blood inlet which receives blood to be cleaned and a first blood outlet which expels partially cleansed blood, the first dialysate compartment having a first dialysate inlet and a first dialysate outlet, said first dialysate inlet for receiving said heated dialysate; and a second dialyzer including a second semi-permeable membrane defining a second blood compartment and a second dialysate compartment, the second blood compartment having a second blood inlet which receives a fluid including at least said partially cleansed blood and a second blood outlet which expels cleaned blood, the second dialysate compartment having a second dialysate inlet and a second dialysate outlet, said second dialysate inlet for receiving dialysate from said source at a temperature lower than a temperature of said heated dialysate that is delivered to the first dialysate inlet.

2. A system according to claim 1, wherein said source of dialysate fluid is fluidly connected to said second dialysate inlet and said heating control module so that dialysate fluid at said lower temperature is delivered to said second dialysate inlet and dialysate fluid delivered to said heating control module is heated prior to delivery to said first dialysate inlet.

3. A system according to claim 1, further comprising:
a mixing chamber which receives said dialysate at an elavated temperature from said heating control module and said lower temperature dialysate from said second dialysate outlet to form said heated dialysate, said heated dialysate being delivered to said first dialysate inlet and having a temperature greater than a temperature of said dialysate from said source.

4. A system according to claim 1, wherein said blood in said first blood compartment has a first temperature and said blood in said second blood compartment has a second temperature, said first temperature being greater than said second temperature.

5. A system according to claim 4, wherein said blood enters said first blood compartment with a temperature less than said first temperature and is heated to said first temperature because of the presence of said heated dialysate fluid within said first dialyzer.

6. A system according to claim 3, wherein said heated dialysate has a temperature greater than about 40 degree C.

7. A system according to claim 1, wherein said fluid comprises said at least partially cleansed blood and substitution fluid.

8. A system according to claim 1, wherein said partially cleansed blood has a first temperature which is greater than a second temperature of said cleaned blood when said cleaned blood exits said second dialyzer.

9. A system according to claim 1, wherein said dialysate is heated by one of adding a secondary fluid at an elevated temperature to said dialysate and passing said dialysate through a heating element disposed in said module.

10. A system according to claim 1, further comprising:
a sterile substitution assembly for mixing sterile substitution fluid with said partially cleansed blood exiting said first dialyzer to form a blood/substitution fluid mixture which is then introduced into said second dialyzer through said second blood inlet.

11. A blood cleansing system comprising: a source of dialysate fluid; a heating control module for producing heated dialysate fluid; a first dialyzer including a first semi-permeable membrane defining a first blood compartment and a first dialystate compartment, the first blood compartment having a first blood inlet which receives blood to be cleaned and a first blood outlet which expels partially cleansed blood, the first dialysate compartment having a first dialysate inlet and a first dialysate outlet, said dialysate inlet for receiving said heated dialysate; a second dialyzer including a second semi-permeable membrane defining a second blood compartment and a second dialystate compartment, the second blood compartment having a second blood inlet which receives a fluid including at least said partially cleansed blood and a second blood outlet which expels cleaned blood, the second dialysate compartment having a second dialysate inlet and a second dialysate outlet, said second dialysate inlet for receiving dialysate at a temperature lower than a temperature of said heated dialysate; and wherein said source of dialysate fluid is connected to said second dialysate inlet for delivering said dialysate thereto, said heating control module being connected to said second dialysate outlet and said first dialysate inlet so that said dialysate flows from said second dialysate outlet to said heating control module where it is heated to form said heated dialysate which is then delivered to said first dialysate inlet.

12. A method of cleaning blood, the method comprising: providing a source of dialysate fluid; providing a first dialyzer including a first semi-permeable membrane defining a first blood compartment and a first dialysate compartment, the first blood compartment having a first blood inlet and a first blood outlet, the first dialysate compartment having a first dialysate inlet and a first dialysate outlet; providing a second dialyzer including a second semi-permeable membrane defining a second blood compartment and a second dialysate compartment, the second blood compartment having a second blood inlet and a second blood outlet, the second dialysate compartment having a second dialysate inlet and a second dialysate outlet; heating at least a portion of said dialysate from said source to produce heated dialysate which is delivered to said first dialysate inlet; delivering dialysate from said source to said second dialysate inlet at a temperature lower than a temperature of said heated dialysate; providing a blood inflow to said first blood inlet; dialyzing said blood inflow in said first dialyzer to provide partially cleaned blood which is delivered to said second blood inlet of said second dialyzer; dialyzing said partially cleansed blood in said second dialyzer to produce cleaned blood; said partially cleansed blood entering said second dialyzer through said second blood inlet, said cleaned blood exiting said second dialyzer through said second dialysate outlet.

13. A method according to claim 12, further comprising:
diafiltering said blood inflow in said first dialyzer to provide partially diafiltered blood which is delivered to said second blood inlet of said second dialyzer; and
diafiltering said partially diafiltered blood in said second dialyzer to produce cleaned blood.

14. A method according to claim 12, wherein heating said dialysate comprises:
passing said dialysate through a heating element disposed in a heating control module.

15. A method according to claim 12, wherein said dialysate is heated to a temperature greater than about 40 degree C.

16. A method according to claim 12, wherein said blood inflow is dialyzed in said first dialyzer at a first temperature greater than a starting temperature of said blood inflow prior to entering said first blood inlet, said partially cleansed blood being dialyzed in said second dialyzer at a temperature substantially equal to said starting temperature.

17. A method according to claim 12, wherein said dialysate is heated to a temperature which is sufficient to cause a temperature of said blood inflow to increase so that an increase in solute diffusivity and a corresponding increase in removal of blood substances by diffusion is realized during said dialysis of said blood in said first and second dialyzers.

18. A method according to claim 13, wherein said dialysate is heated to a temperature which is sufficient to cause a temperature of said blood inflow to increase so that enhanced convection, due to higher filtration of lower viscosity plasma water, is realized during said diafiltration in said first and second dialyzers.

19. A method according to claim 12, further comprising:
mixing said dialysate fluid from said second dialysate outlet with said heated dialysate to form a mixed dialysate fluid having an elevated temperature relative to said temperature of said dialysate source; and
introducing said mixed dialysate fluid into said first dialysate inlet.

20. A method according to claim 12, further comprising:
mixing sterile substitution fluid with said partially cleansed blood exiting said first dialyzer to form a blood/substitution fluid mixture which is then introduced into the second dialyzer through said second blood inlet.

21. A method according to claim 12, wherein said source of dialysate fluid is connected to said second dialysate inlet, said dialysate flowing from said second dialysate outlet to a heating control module where said dialysate is heated to produce said heated dialysate which is then delivered to said first dialysate inlet.

22. A method according to claim 12, further comprising:
   delivering a portion of said dialysate from said source to said second dialysate inlet; and
   diverting a portion of said dialysate to a heating control module which heats said dialysate to produce said heated dialysate.

23. A method of cleansing blood, the method comprising: supplying a source of dialysate fluid and a blood inflow; diafiltering said blood inflow in a first dialyzer to provide partially diafiltered blood, said first dialyzer including a first semi-permeable membrane defining a first blood compartment and a first dialysate compartment, the first blood compartment having a first blood inlet receiving said blood inflow and a first blood outlet, the first dialysate compartment having a first dialysate inlet and a first dialysate outlet, said dialysate in said first dialysate compartment having a first elevated temperature so that said blood inflow is diafiltered at an elevated temperature; and diafiltering said partially diafiltered blood in a second dialyzer to provide cleansed blood, said second dialyzer including a second semi-permeable membrane defining a second blood compartment and a second dialysate compartment, the second blood compartment having a second blood inlet receiving said partially diafiltered blood and a second blood outlet, the second dialysate compartment having a second dialysate inlet and a second dialysate outlet, said dialysate in said second dialysate compartment having a second temperature less than said first temperature, said cleansed blood having a temperature which is less than said elevated temperature of said partially diafiltered blood.

24. A method according to claim 23, wherein said diafiltering of said blood inflow comprises:
   diffusing a portion of said blood inflow by a first countercurrent of said dialysate having said elevated temperature and in diffusion communication with said blood inflow, and wherein said diafiltering said partially diafiltered blood comprises diffusing a portion of said partially diafiltered blood by a second countercurrent of said dialysate of said second temperature and in diffusion communication with said partially diafiltered blood.

* * * * *